United States Patent
Ichiki et al.

(10) Patent No.: US 10,301,682 B2
(45) Date of Patent: *May 28, 2019

(54) FLUIDIC DEVICE, EXOSOME ANALYSIS METHOD, BIOMOLECULE ANALYSIS METHOD, AND BIOMOLECULE DETECTION METHOD

(71) Applicants: The University of Tokyo, Bunkyo-ku, Tokyo (JP); Nikon Corporation, Chiyoda-ku, Tokyo (JP)

(72) Inventors: Takanori Ichiki, Tokyo (JP); Masashi Kobayashi, Tokyo (JP); Ayako Hayashi, Kuki (JP); Shoichi Tsuchiya, Chigasaki (JP); Takanori Akagi, Tokyo (JP); Taro Ueno, Tokyo (JP); Takashi Funatsu, Tokyo (JP); Kenji Miyamoto, Yokohama (JP)

(73) Assignees: THE UNIVERSITY OF TOKYO, Tokyo (JP); NIKON CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/080,266

(22) Filed: Mar. 24, 2016

(65) Prior Publication Data
US 2016/0230235 A1    Aug. 11, 2016

Related U.S. Application Data

(63) Continuation of application No. PCT/JP2014/071422, filed on Aug. 14, 2014.

(30) Foreign Application Priority Data

Sep. 25, 2013  (JP) ................. 2013-199070

(51) Int. Cl.
*C12Q 1/6886*  (2018.01)
*G01N 33/53*  (2006.01)
(Continued)

(52) U.S. Cl.
CPC .......... *C12Q 1/6886* (2013.01); *B01L 3/5027* (2013.01); *B01L 3/502715* (2013.01);
(Continued)

(58) Field of Classification Search
CPC .. C12M 1/00; B01L 3/502715; C12Q 1/6886; G01N 15/06
See application file for complete search history.

(56) References Cited

U.S. PATENT DOCUMENTS 7,230,092 B2 * 6/2007 Bortolin ............... C12Q 1/6813
435/6.12
7,754,475 B2 * 7/2010 Wang .................. C12Q 1/6834
422/425

(Continued)

FOREIGN PATENT DOCUMENTS

JP    2011-510309 A    3/2011
JP    2012-127696 A    7/2012

(Continued)

OTHER PUBLICATIONS

Akagi et al, Immobilization and isolation of exosomes using polyethylene glycol-lipid-modified surface in a microchannel and evaluation by atomic force microscopy, 2012, 16th International Conference on Miniaturized Systems for Chemistry and Life Sciences, MicroTAS 2012—Okinawa, pp. 1 and 2.*

(Continued)

*Primary Examiner* — Narayan K Bhat
(74) *Attorney, Agent, or Firm* — Squire Patton Boggs (US) LLP

(57) ABSTRACT

The present invention provides a fluidic device, an exosome analysis method, a biomolecule analysis method, and a biomolecule detection method, which can analyze even the content of an exosome in a series of flows by introducing a sample into the device. A fluidic device of the present (Continued)

invention is a fluidic device which detects a biomolecule contained in an exosome in a sample, and includes: an exosome purification unit which has a layer modified with a compound having a hydrophobic chain and a hydrophilic chain; a biomolecule purification unit; a biomolecule detection unit; a first flow path which connects the exosome purification unit to the biomolecule purification unit; and a second flow path which connects the biomolecule purification unit to the biomolecule detection unit.

13 Claims, 9 Drawing Sheets

Specification includes a Sequence Listing.

(51) Int. Cl.
  *B01L 3/00* (2006.01)
  *C12Q 1/6806* (2018.01)
(52) U.S. Cl.
  CPC ...... *B01L 3/502761* (2013.01); *C12Q 1/6806* (2013.01); *G01N 33/5308* (2013.01); *B01L 2200/0631* (2013.01); *B01L 2200/10* (2013.01); *B01L 2300/0627* (2013.01); *B01L 2300/0816* (2013.01); *B01L 2300/0861* (2013.01); *B01L 2300/0864* (2013.01); *B01L 2300/0867* (2013.01); *B01L 2300/161* (2013.01); *B01L 2300/165* (2013.01); *B01L 2400/0487* (2013.01); *C12Q 2600/158* (2013.01); *C12Q 2600/16* (2013.01); *C12Q 2600/178* (2013.01)

(56) References Cited

U.S. PATENT DOCUMENTS

| | | | | |
|---|---|---|---|---|
| 8,551,714 | B2* | 10/2013 | Jovanovich | B01F 11/0071 422/502 |
| 2010/0184046 | A1* | 7/2010 | Klass | C12Q 1/6886 435/7.1 |
| 2010/0298151 | A1* | 11/2010 | Taylor | C12Q 1/6809 506/2 |
| 2011/0022324 | A1 | 1/2011 | Knopp et al. | |
| 2013/0260481 | A1 | 10/2013 | Shimizu et al. | |
| 2015/0051105 | A1* | 2/2015 | Ueno | C12Q 1/6834 506/9 |

FOREIGN PATENT DOCUMENTS

| | | |
|---|---|---|
| JP | 2013-102768 A | 5/2013 |
| WO | WO 2009/015357 A1 | 1/2009 |
| WO | WO 2009/092386 A2 | 7/2009 |
| WO | WO2010/065765 * | 10/2010 |
| WO | WO 2012/048372 A1 | 4/2012 |
| WO | WO2012055415 * | 5/2012 |
| WO | WO 2012/081361 A1 | 6/2012 |
| WO | WO2013/153911 * | 10/2013 |

OTHER PUBLICATIONS

Kobayashi et al, date confirmation document, printed Sep. 6, 2018, p. 1-2. (Year: 2012).*
Ichiki. Takanori, "Cancer Diagnostic Platform by microRNA," Gendai Kagaku, Mar. 2013, pp. 42-45 and 76, with partial English translation, 7 pages.
Kobayashi, Masashi et al., "Development of the isolation method for exosome in human serum immobilized by biocompatible anchor for membrane", JSAP Spring Meeting Koen Yokoshu, Mar. 2013, vol. 60, p. 12-194, #29a-G17-10, with partial English translation, 2 pages.
Kobayashi, Masashi et al., "Development of evalution method for immobilized exosomes in human serum on the glass substrate modified with biocompatible anchor for membrane," JSAP Autumn Meeting Koen Yokoshu, Sep. 17, 2013, vol. 74, p. 12-155, #17a-C4-10, with partial English translation, 3 pages.
International Search Report for International Application No. PCT/JP2014/071422, dated Nov. 11, 2014, with English translation, 4 pages.
Written Opinion of the International Search Authority for International Application No. PCT/JP2014/071422, dated Nov. 11, 2014, with English translation, 11 pages.
Office Action for Japanese Patent Application No. 2015-539014, dated May 29, 2018, with English translation (10 pages).
Akagi, et al., Proceedings of 16th International Conference on Minituarized Systems for Chemistry and Life Sciences, Oct. 28, 2012, pp. 1291-1293, with copyright page (available at http://www.rsc.org/images/loc/2012/html/Copyright.html).
Charafe-Jauffret, E. et al., "Gene expression profiling of breast cell lines identifies potential new basal markers," Oncogene, 2006, vol. 25, pp. 2273-2284.
Kobayashi, Masashi et al., "Development of the microfluidic device for exsome isolation," Proceedings of the 73$^{rd}$ Autumn Meeting, 2012, The Japan Society of Applied Physics, Aug. 27, 2012, p. 12-160, with English translation, 2 pages.
International Search Report for International Application No. PCT/JP2014/072252, dated Nov. 25, 2014, with English translation, 4 pages.
Written Opinion of the International Search Authority for International Application No. PCT/JP2014/072252, dated Nov. 25, 2014, with English Translation, 9 pages.
Office Action dated Nov. 29, 2018 for U.S. Appl. No. 15/053,345, 17 pages.
Notice of Reason For Rejection dated Dec. 4, 2018 for Japanese Patent Application No. 2015-539014, with English translation, 8 pages.

* cited by examiner

| R | 5951 | R | 5952 | R | 5953 |
|---|---|---|---|---|---|
| 6022 | S | 6033 | S | 6033 | S |
| T | 6110 | T | 6111 | T | 6112 |
| 6191 | U | 6192 | U | 6193 | U |
| C-prot | 6270 | C-prot | 6271 | C-prot | 6272 |
| 6351 | A | 6352 | A | 6353 | A |
| B | 6430 | B | 6432 | B | 6433 |
| 6511 | C | 6512 | C | 6513 | C |
| D | 6591 | D | 6592 | D | 6593 |
| 6672 | E | 6673 | E | 6674 | E |
| F | 6752 | F | 6753 | F | 6754 |

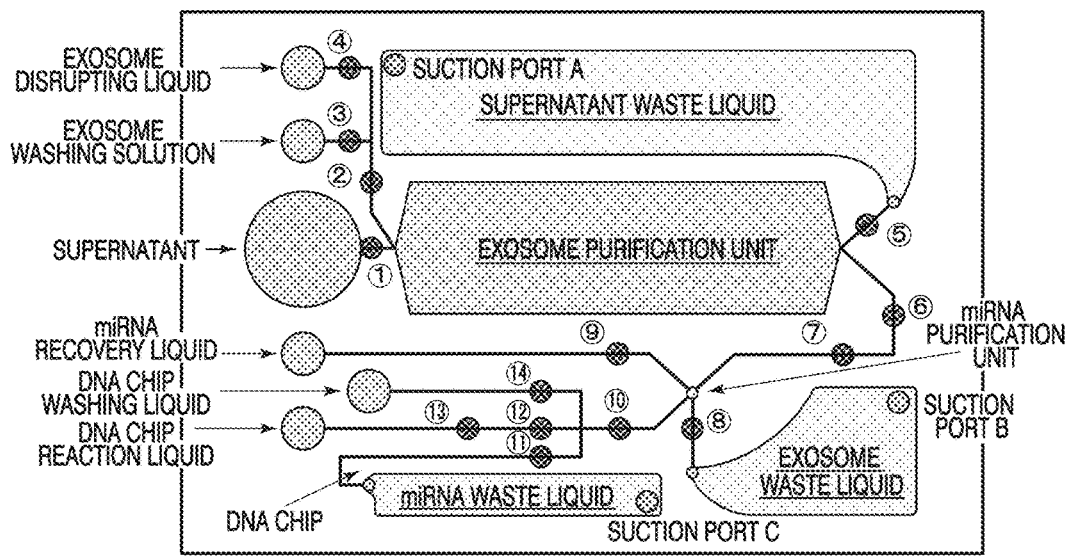

ered to as miRNA) from a biological sample and determining the amount of predetermined miRNA expressed in the cancer cell-derived exosomes, and then, comparing such amount of predetermined miRNA with the amount of miRNA expressed in a specimen-derived exosomes has been proposed (refer to Patent Document 1).

DESCRIPTION OF RELATED ART

Patent Document

Patent Document 1: JP2013-102768A

SUMMARY OF THE INVENTION

Although Patent Document 1 describes the steps, which are performed by researchers, of isolating an exosome, purifying miRNA from the exosome, and analyzing the miRNA, there is no disclosure in Patent Document 1 of a technology capable of analyzing even the content of the exosome in a series of flows only by introducing a sample into a device, and thus, there is room for improvement.

The present invention has been made in consideration of the above-described circumstances, and an object of the present invention is to provide a fluidic device, an exosome analysis method, a biomolecule analysis method, and a biomolecule detection method which can analyze even the content of an exosome in a series of flows only by introducing a sample into the device.

The present inventors have conducted extensive studies in order to solve the above-described problems, and as a result, they have found that the problems can be solved using an exosome purification unit which has a layer modified with a compound having a hydrophilic chain and a hydrophobic chain. An embodiment of the present invention provides the following (1) to (5).

(1) A fluidic device in an embodiment of the present invention which detects a biomolecule contained in an exosome in a sample comprises:
 an exosome purification unit having an exosome immobilization unit which has a layer modified with a compound having a hydrophobic chain and a hydrophilic chain;
 a biomolecule purification unit;
 a biomolecule detection unit;
 a first flow path which connects the exosome purification unit to the biomolecule purification unit; and
 a second flow path which connects the biomolecule purification unit to the biomolecule detection unit.

(2) A fluidic device in an embodiment of the present invention which purifies a biomolecule contained in an exosome in a sample comprises:
 a sample introduction inlet and an exosome-disrupting liquid introduction inlet.

(3) A method of analyzing an exosome in an embodiment of the present invention comprises: a step of purifying and disrupting an exosome on an exosome purification unit which has a layer modified with a compound having a hydrophilic chain and a hydrophobic chain.

(4) A method of analyzing a biomolecule in an embodiment of the present invention comprises:
 (a) a step of bringing an exosome-containing sample into contact with a substrate which is modified with a compound which has a hydrophobic chain and a hydrophilic chain in a fluidic device, to immobilize the exosome by the compound which has a hydrophobic chain and a hydrophilic chain on the substrate;
 (b) a step of releasing a biomolecule contained in the exosome by disrupting the exosome after a disrupting liquid has been introduced to the substrate to which the exosome is immobilized;
 (c) a step of purifying the biomolecule; and
 (d) a step of detecting the biomolecule.

(5) A method of detecting a biomolecule in an embodiment of the present invention comprises:
 (a) a step of bringing a sample, which includes a structure surrounded by a lipid bilayer, into contact with a substrate modified with a compound having a hydrophobic chain and a hydrophilic chain, to immobilize the structure surrounded by the lipid bilayer by the compound having a hydrophobic chain and a hydrophilic chain on the substrate;

(b) a step of releasing a biomolecule contained in the structure surrounded by the lipid bilayer by disrupting the structure surrounded by the lipid bilayer; and (d) a step of detecting the biomolecule.

According to the present invention, it is possible to analyze even the content of an exosome in a series of flows only by introducing a sample into a device.

BRIEF DESCRIPTION OF THE DRAWINGS

FIG. 9A is a schematic view of an aspect of a fluidic device in the present embodiment.

FIG. 9B is a result showing the details of controlling a valve in a fluidic device in Example.

DETAILED DESCRIPTION OF THE INVENTION

Fluidic Device

First Embodiment

Figure 1:
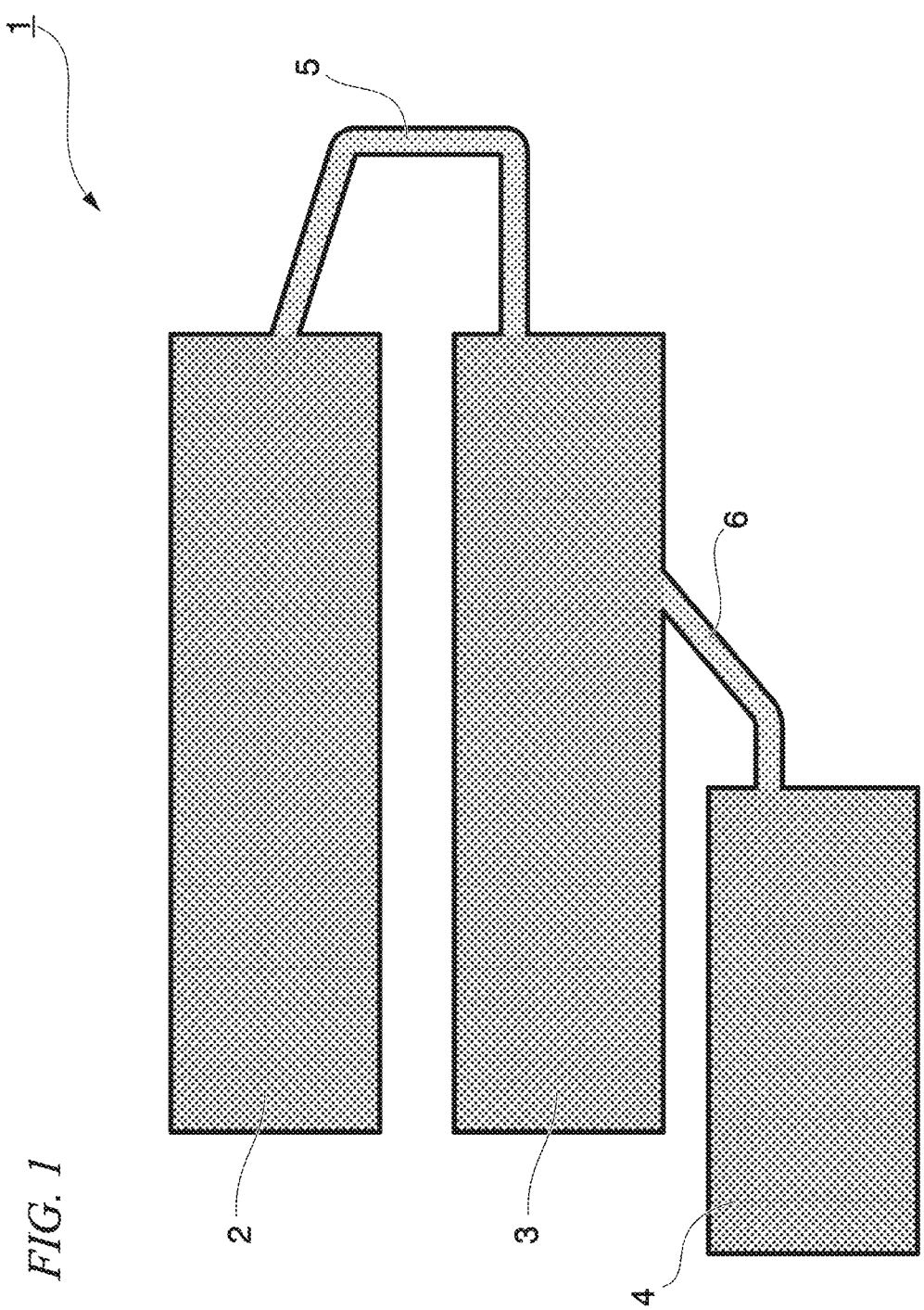
FIG. 1 is a schematic view of an aspect of a fluidic device in the present embodiment.

As shown in FIG. 1, a fluidic device (for example, a microfluidic device (μTAS) or a millimetric fluidic device (mTAS)) 1 of the present embodiment comprises: an exosome purification unit 2 which has a layer modified with a compound having a hydrophobic chain and a hydrophilic chain; a biomolecule purification unit 3; a biomolecule detection unit 4; a first flow path 5 which connects the exosome purification unit 2 to the biomolecule purification unit 3; and a second flow path 6 which connects the biomolecule purification unit 3 to the biomolecule detection unit 4.

The fluidic device 1 of the present embodiment is a device which detects a biomolecule contained in an exosome in a sample.

In the present embodiment, the first flow path 5 is a flow path which sends an exosome-disrupting liquid containing a biomolecule to the biomolecule purification unit 3 from the exosome purification unit 2, and the second flow path 6 is a flow path which sends a solution containing the purified biomolecule to the biomolecule detection unit 4.

In addition, the fluidic device 1 of the present embodiment is a device of detecting a biomolecule by introducing a sample into the device, disrupting an exosome, and purifying a biomolecule, using, for example, the structure shown in FIG. 9(A) to be described below.

An exosome is a small lipid vesicle with a diameter of 30 nm to 100 nm which is surround by a lipid bilayer membrane, and is secreted into a body fluid such as blood, urine, and saliva from various cells such as a tumor cell, a dendritic cell, a T cell, and a B cell, as a fused body of an endosome and a cell membrane.

The exosome is a secretion of a cell and contains biomolecules, for example, proteins, nucleic acids, and miRNA, which are derived from the cell of a secretion source. An abnormal cell such as a cancer cell existing within a living body expresses unique proteins, nucleic acids, miRNA, or the like within a cell membrane of the exosome.

For this reason, it is possible to detect an abnormality of a cell of a secretion source by analyzing a biomolecule contained in an exosome. Examples of means for taking out (extracting) a biomolecule contained in an exosome include disrupting of a lipid bilayer membrane of the exosome.

Furthermore, the exosome is detected in a body fluid, such as blood, urine, and saliva, circulating within a living body. Therefore, it is possible to detect an abnormality within a living body by analyzing the exosome without performing a biopsy examination.

It is preferable that the fluidic device 1 of the present embodiment further comprises a waste liquid tank from the viewpoint of preventing a secondary infection due to a sample used in analysis. For example, as shown in FIG. 2, the fluidic device of the present embodiment comprises a first waste liquid tank 7, a second waste liquid tank 8, and a third waste liquid tank 9, and preferably comprises: a third flow path 10 which connects the first waste liquid tank 7 to the exosome purification unit 2; a fourth flow path 11 which connects the second waste liquid tank 8 to the biomolecule purification unit 3; and a fifth flow path 12 which connects the third waste liquid tank 9 to the biomolecule detection unit 4.

Figure 2:
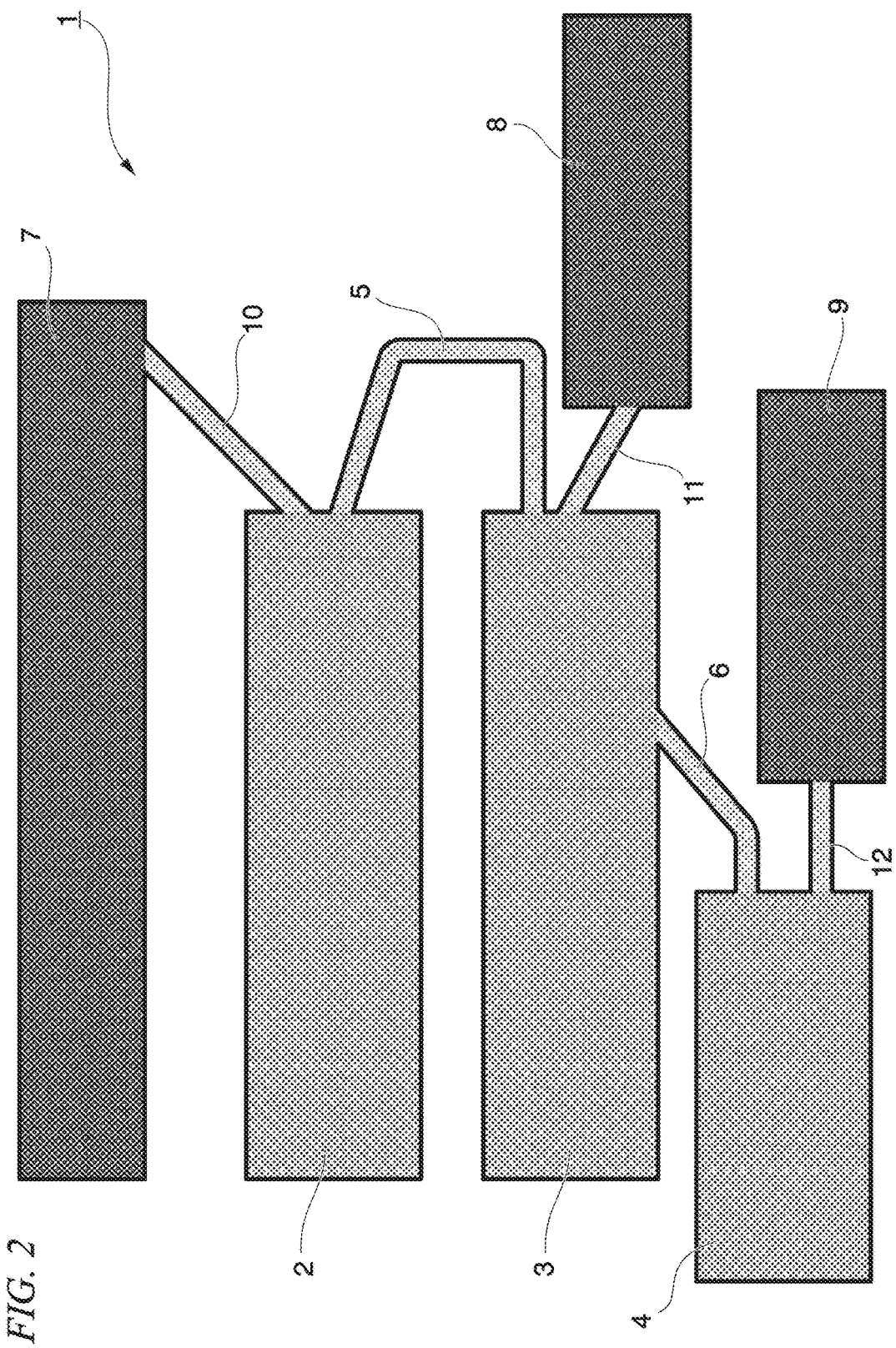
FIG. 2 is a schematic view of an aspect of the fluidic device in the present embodiment.

There are three waste liquid tanks shown in FIG. 2. However, the waste liquid tanks may be combined in one or two waste liquid tanks.

As will be described below, a waste liquid from the exosome purification unit 2 is sent to the first waste liquid tank 7 through the third flow path 10. A waste liquid from the biomolecule purification unit 3 is sent to the second waste liquid tank 8 through the fourth flow path 11. A waste liquid from the biomolecule detection unit 4 is sent to the third waste liquid tank 9 through the fifth flow path 12.

An example of each configuration in the fluidic device 1 of the present embodiment will be described using FIG. 3.

The exosome purification unit 2 performs immobilization of an exosome and disrupting of an exosome, and comprises an inlet, and an exosome immobilization unit 2d which has the layer modified with the compound having a hydrophobic chain and a hydrophilic chain. It is preferable that the exosome purification unit 2 comprises an inlet for each reagent to be introduced, as shown in FIG. 3. That is, it is preferable that the exosome purification unit 2 comprises a sample introduction inlet 2b and a disrupting liquid introduction inlet 2c, and it is more preferable that the exosome purification unit further comprises a washing solution introduction inlet 2a.

The compound which has a hydrophobic chain and a hydrophilic chain in the exosome immobilization unit 2d is a compound having a hydrophobic chain in order to be immobilized to a lipid double membrane, and a hydrophilic chain in order to dissolve this lipid chain. With use of the compound, it is possible to immobilize an exosome having a lipid double membrane on the exosome immobilization unit 2d.

In the present specification, the expression "immobilization of an exosome on the exosome immobilization unit 2d" also means adsorption of an exosome on the exosome immobilization unit. It is possible to isolate an exosome from a sample.

The hydrophobic chain may be a single chain or a plurality of chains, and examples thereof include a saturated or unsaturated hydrocarbon group which may have a substituent group.

As the saturated or unsaturated hydrocarbon group, a 6-24C straight-chain or branched-chain alkyl group or alkenyl group is preferable, and examples thereof include a hexyl group, a heptyl group, an octyl group, a nonyl group, a decyl group, an undecyl group, a dodecyl, a tridecyl group, a tetradecyl group, a pentadecyl group, a hexadecyl group, a heptadecyl group, a stearyl group (octadecyl group), a nonadecyl group, an icosyl group, a henicosyl group, a docosyl group, a tricosyl group, a tetracosyl group, a myristoleyl group, a palmitoleyl group, an oleyl group, a linoyl group, a linoleyl group, a ricinoleyl group, and an isostearyl group.

Among these, a myristoleyl group, a palmitoleyl group, an oleyl group, a linoyl group, and a linoleyl group are preferable, and an oleyl group is more preferable.

Examples of the hydrophilic chain include proteins, oligopeptides, polypeptides, polyacrylamide, polyethylene glycol (PEG), and dextran, and PEG is preferable. The hydrophilic chain is preferably modified chemically for bonding to a substrate, more preferably has an active ester group, and particularly preferably has an N-hydroxysuccinimide group.

That is, as the compound having a hydrophobic chain and a hydrophilic chain, a lipid-PEG derivative is preferable. The lipid-PEG derivative is called a biocompatible anchor for membrane (BAM). Examples of the BAM include a compound represented by the following Formula (1).

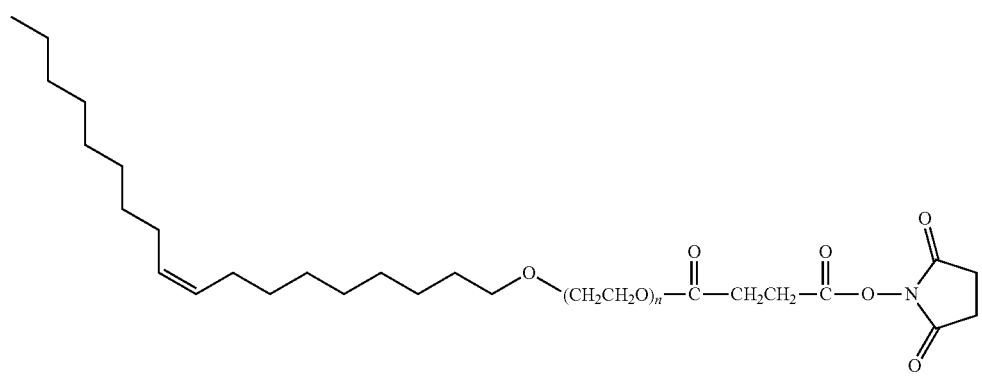

(1)

[In Formula, n represents an integer greater than or equal to 1.]

Examples of the substrate used as a layer of the exosome immobilization unit 2d include a glass substrate, a silicon substrate, a polymer substrate, and a metal substrate. The bonding of a substrate may be performed through a substance bonding to a hydrophilic chain of the compound having a hydrophobic chain and a hydrophilic chain. Examples of the substance include a substance having an amino group, a carboxyl group, a thiol group, a hydroxyl group, or an aldehyde group, and 3-aminopropyltriethoxysilane is preferable.

Driving of a liquid in the fluidic device 1 of the present embodiment is performed by an external suction pump, and the flow of the liquid is controlled by opening and closing a valve. Examples of the valve include a pneumatic valve, and the opening and closing of the valve is driven and controlled by an external pneumatic device which is connected to the fluidic device 1.

Figure 3:
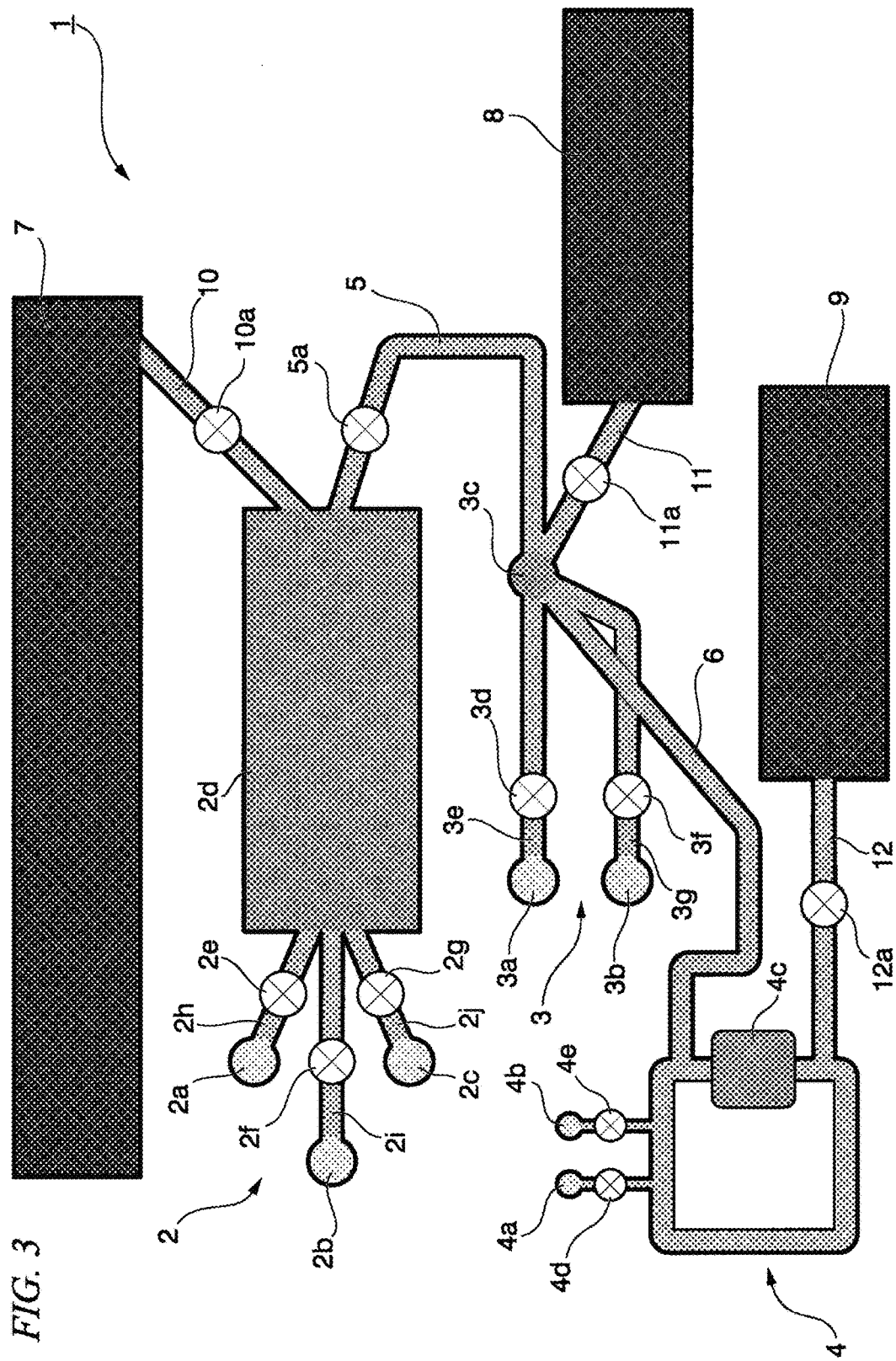
FIG. 3 is a schematic view of an aspect of the fluidic device in the present embodiment.

As shown in FIG. 3, in the analysis of an exosome, a sample is first injected into the sample introduction inlet 2b in the above-described exosome purification unit, and the sample is introduced into the exosome immobilization unit 2d through suctioning, after opening a valve 2f of a flow path 2i.

Examples of the amount of the sample used in the analysis include several μL to several mL. For example, the amount of the sample is about 1 mL.

The sample is not particularly limited as long as the sample can be obtained from an environment surrounding a cell to be detected and contains an exosome secreted by the cell, and examples thereof include blood, urine, breast milk, bronchoalveolar lavage fluid, amniotic fluid, a malignant effusion, or saliva. Among these, blood or urine from which it is easy to detect an exosome is preferable. Furthermore, in blood, blood plasma is preferable in view of ease of detection of an exosome.

In addition, the sample also includes a cell culture solution which contains an exosome secreted by a culture cell.

Examples of the cell to be detected include a cancer cell, a mast cell, a dendritic cell, a reticulocyte, an epithelial cell, a B cell, and a neuron, which are known to produce an exosome.

The sample may be prepared through ultracentrifugation, ultrafiltration, continuous flow electrophoresis, filtration using a size filter, gel filtration chromatography, or the like. However, in the present embodiment, the affinity between an exosome and a compound having a hydrophobic chain and a hydrophilic chain in the exosome immobilization unit 2d is significantly high, and therefore, the sample may be a sample itself which has not been processed.

It is preferable to provide a non-specific adsorption suppression unit to the exosome immobilization unit 2d from the viewpoint of specifically bonding an exosome to the exosome immobilization unit 2d. Examples of the method thereof include a method of modifying a substrate with a compound having a hydrophobic chain and a hydrophilic chain, and then, treating a site which is not modified with the compound having a hydrophobic chain and a hydrophilic chain, with a compound having a hydrophilic chain such as PEG.

An exosome in a sample which has been introduced into the exosome immobilization unit 2d is captured by the above-described compound having a hydrophobic chain and a hydrophilic chain. The affinity between the exosome and the compound having a hydrophobic chain and a hydrophilic chain is significantly high. Therefore, exosomes in samples are captured on the exosome immobilization unit 2d at the same time when the samples continuously pass through the top of the exosome immobilization unit 2d without allowing the samples to stand in the exosome immobilization unit 2d.

For example, the suction pressure during the capturing of an exosome is 1 kPa to 30 kPa and the time required for the capturing is about 15 seconds. A solution which has been passed through the exosome immobilization unit 2d is sent to the first waste liquid tank 7 after passing through the third flow path 10 via the valve 10a.

In the fluidic device 1 of the present embodiment, it is preferable to design the ceiling height of the exosome immobilization unit 2d to be low. Accordingly, the opportunity of contact between an exosome and a compound having a hydrophobic chain and a hydrophilic chain is increased, and therefore, it is possible to improve the capturing efficiency of an exosome.

In blood, extracellular vesicles such as microvesicles or apoptotic bodies are contained in addition to the exosome, and there is a possibility that these extracellular vesicles will be immobilized to the exosome immobilization unit 2d. From the viewpoint of removing these extracellular vesicles from the exosome immobilization unit 2d, it is preferable to wash an exosome on the exosome immobilization unit 2d.

For example, as shown in FIG. 3, a washing solution is injected into the washing solution introduction inlet 2a after opening the valve 2e on the flow path 2h, and is introduced into the exosome immobilization unit 2d.

In the present embodiment, the bonding of the exosome to the layer modified with the compound having a hydrophilic chain and a hydrophobic chain is strong. Therefore, it is possible to adjust the flow velocity to be fast and to perform washing in a short period of time. For example, washing is performed by sending 500 μL of a PBS washing solution for about 15 seconds at a suction pressure of 1 kPa to 30 kPa. A waste liquid which has been passed through the exosome immobilization unit 2d is sent to the first waste liquid tank 7 after passing through the third flow path 10 via the valve 10a.

Next, the exosome which has been immobilized on the exosome immobilization unit 2d is disrupted. As shown in FIG. 3, a disrupting liquid is injected into the disrupting liquid introduction inlet 2c and is introduced into the exosome immobilization unit 2d through suctioning, after opening a valve 2g on a flow path 2j. Examples of the disrupting liquid include a known liquid in the related art which is used in dissolving a cell.

The exosome which has been captured on the exosome immobilization unit 2d is disrupted by the disrupting liquid passing through the exosome immobilization unit 2d, and a biomolecule contained in the exosome is released.

For example, the suction pressure during the disrupting of an exosome is 1 kPa to 30 kPa and the time required for the disrupting is about 30 seconds. A waste liquid which has been passed through the exosome immobilization unit 2d is sent to the first waste liquid tank 7 after passing through the third flow path 10 via the valve 10a. The biomolecule which has been released from the exosome is sent to the biomolecule purification unit 3 after passing through the first flow path 5 via a valve 5a.

As shown in FIG. 3, the biomolecule purification unit 3 preferably comprises a biomolecule recovery liquid introduction inlet 3b and a biomolecule immobilization unit 3c, and more preferably further comprises a biomolecule washing solution introduction inlet 3a.

The biomolecule immobilization unit 3c is not particularly limited as long as the biomolecule immobilization unit can immobilize a biomolecule, and examples thereof include a silica membrane which immobilizes a nucleic acid, in a case where the biomolecule is a nucleic acid.

An exosome holds a protein or a nucleic acid which is derived from a cell as a secretion source. Examples of the nucleic acid include miRNA. In recent years, it has been reported that miRNA which is a non-coding RNA with a short chain suppresses gene expression within a living body, and the relationship between abnormal expression of miRNA and various diseases starting from cancer is becoming clear.

In the present embodiment, it is preferable that a biomolecule which is immobilized by the biomolecule immobilization unit 3c is miRNA. Examples of the biomolecule immobilization unit 3c include a silica membrane embedded on the flow path, as described above.

An exosome-disrupting liquid passes through the biomolecule immobilization unit 3c, and a biomolecule is captured on the biomolecule immobilization unit 3c.

For example, the suction pressure during the sending of an exosome-disrupting liquid is 50 kPa to 70 kPa and the time required for the sending is about 1 minute. A waste liquid which has been passed through the biomolecule immobilization unit 3c is sent to the second waste liquid tank 8 after passing through the fourth flow path 11 via a valve 11a.

After immobilizing a biomolecule on the biomolecule immobilization unit 3c, it is preferable to remove impurities other than the target biomolecule by washing the biomolecule immobilization unit 3c.

As shown in FIG. 3, a valve 3d on a flow path 3e is opened, a washing solution is injected into the biomolecule washing solution introduction inlet 3a, and a washing solution is introduced into the biomolecule immobilization unit 3c through suctioning. Examples of the washing solution include ethanol at about 70% to 80%.

For example, the amount of washing solution to be used during washing is about 1 mL, the suction pressure is 50 kPa to 70 kPa, and the time required for sending a washing solution is about 1 minute. A waste liquid which has been passed through the biomolecule immobilization unit 3c is sent to the second waste liquid tank 8 after passing through the fourth flow path 11 via the valve 11a. The biomolecule which has been released from the exosome is sent to the biomolecule purification unit 3 after passing through the first flow path 5 via the valve 5a.

In order to prevent the biomolecule washing solution from being brought into the biomolecule detection unit, it is preferable to dry the biomolecule immobilization unit 3c after washing the biomolecule immobilization unit 3c.

As shown in FIG. 3, drying of the biomolecule immobilization unit is performed by suctioning air from the biomolecule washing solution introduction inlet 3a and passing the air through the biomolecule immobilization unit 3c.

For example, the suction pressure during the drying of the biomolecule immobilization unit 3c is 50 kPa to 70 kPa and the time required for drying is about 2 minutes.

Next, the biomolecule which has been immobilized on the biomolecule immobilization unit 3c is eluted. In order to improve the recovery rate of the biomolecule, it is preferable to hold a biomolecule recovery liquid for a certain time after introducing the biomolecule recovery liquid into the biomolecule immobilization unit 3c.

As shown in FIG. 3, the biomolecule recovery liquid is injected into the biomolecule recovery liquid introduction inlet 3b after opening a valve 3f of a flow path 3g, and is introduced into the biomolecule immobilization unit 3c.

For example, the biomolecule recovery liquid is RNase-free water, the amount of the recovery liquid used is 30 μL, the recovery liquid is suctioned at a suction pressure of 50 kPa to 70 kPa, the suctioning is stopped at a point in time at which the recovery liquid has reached the biomolecule immobilization unit 3c, and the recovery liquid is held for about 3 minutes.

Next, the biomolecule is recovered from the biomolecule immobilization unit 3c. For example, the recovery liquid is recovered for 30 seconds at a suction pressure of 50 kPa to 70 kPa.

The biomolecule is sent to the biomolecule detection unit 4 through the second flow path 6. For example, the suction pressure of the biomolecule into the biomolecule detection unit 4 is less than or equal to 6 kPa, and the biomolecule is sent to the biomolecule detection unit for about 30 seconds.

The biomolecule detection unit 4 comprises, for example, a substrate to which a substance having affinity to the biomolecule is immobilized. For example, the biomolecule detection unit preferably comprises a nucleic acid array in a case where the biomolecule is a nucleic acid, and the biomolecule detection unit preferably comprises a protein array in a case where the biomolecule is a protein. The biomolecule detection unit preferably comprises a substrate 4c to which a probe complementary to target miRNA is immobilized (refer to FIG. 3) in a case where the biomolecule is miRNA. Examples of the substrate to which a probe complementary to target miRNA is immobilized include a DNA chip which is known in the related art.

Furthermore, it is preferable that the biomolecule detection unit 4 comprises the following configuration from the viewpoint of specifically detecting target miRNA with high sensitivity.

In a case where target miRNA 33 includes a first section 31 and a second section 32 as shown in FIGS. 9(A) and 9(B), it is preferable that the biomolecule detection unit 4 comprises a substrate, to which a capture probe 34 including a sequence which can be hybridized with the first section 31 is immobilized, and a detection probe introduction inlet 4a (refer to FIG. 3).

A detection probe 35 comprises: two stem sections 35c and 35d forming a double stranded structure; a loop section 35e which is a region between the two stem sections 35c and 35d and is labeled using a labeling substance 35a; and a sequence 35b that can be hybridized with the second section 32 in a case where the target miRNA 33 includes the first section 31 and the second section 32; and a 5'-protruding terminus or a 3'-protruding terminus.

The capture probe 34 and the detection probe 35 can respectively be hybridized with the first section 31 and the second section 32 of the miRNA 33. For this reason, the length of the first section 31 and the length of the second section 32 are preferably 5 bases to 17 bases, and more preferably 7 bases to 15 bases from the viewpoint of the number of bases in which miRNA formed of about 22 bases is divided into two.

In the present embodiment, the section on the 5' side of the miRNA 33 is regarded as the first section 31 and the section on the 3' side of the miRNA 33 is regarded as the second section 32.

The expression "can be hybridized" in the present invention and in the present specification means that a part of a capture probe and a part of a detection probe which are used in the present invention are hybridized with a target nucleic acid (target miRNA) under stringent conditions, but are not hybridized with a nucleic acid molecule other than the target nucleic acid (target miRNA). Examples of the "stringent conditions" include conditions disclosed in Molecular Cloning—A Laboratory Manual, Third Edition (Sambrook et al., Cold Spring Harbor Laboratory Press).

The capture probe 34 comprises a sequence which can be hybridized with the first section 31 of the miRNA 33 in a 5'-terminal region.

It is preferable that the capture probe 34 does not comprise a sequence complementary to the second section 32 of the miRNA 33 so as not to be hybridized with the second section 32 of the miRNA 33 from the viewpoint of quantitatively determining the miRNA 33 with high accuracy.

Molecular degrees of freedom are required in order for the capture probe 34 which has been immobilized to the substrate 36 to be hybridized with the miRNA 33. Therefore, it is preferable that the capture probe 34 has, at its 3'-terminus, a spacer 34a, which is immobilized to the substrate 36. The length of the spacer 34a is not particularly limited, but is preferably 3 bases to 50 bases and more preferably 5 bases to 25 bases. However, a base to be used for the spacer can be replaced with a linker such as PEG which has the same length and the same flexibility as that of the base. In that case, the number of bases to be used for the spacer 34a may be 0.

The length of the capture probe 34 is not particularly limited as long as the length is a length required for functioning as a probe, but is preferably 3 bases to 50 bases and more preferably 5 bases to 40 bases in consideration of the number of bases of the first section 31 and the spacer 34a.

The capture probe 34 may be DNA or RNA. The capture probe is not limited to be a natural one or a non-natural one as long as the probe has the same function as that of DNA or RNA and may be one containing an artificial nucleic acid such as a peptide nucleic acid (PNA), a locked nucleic acid (LNA), and a bridged nucleic acid (BNA). It is preferable that the capture probe 34 contains an LNA or a BNA from the viewpoint of higher affinity to the target miRNA 33, being more hardly recognized by DNase or RNase, and being more capable of becoming a substrate for DNA ligase such as T4 DNA ligase, compared to DNA or RNA.

Examples of the substrate 36 used for immobilizing the capture probe 34 include a glass substrate, a silicon substrate, a plastic substrate, and a metal substrate. Examples of the method of immobilizing the capture probe 34 on the substrate 36 include a method of immobilizing a probe on a substrate at high density using photolithographic technology or a method of immobilizing a probe on a glass substrate or the like through spotting.

In the present embodiment, the detection probe 35 comprises the sequence 35b which can be hybridized with the second section 32 of the miRNA 33 in a 3'-terminal region.

It is preferable that the detection probe 35 does not contain a sequence complementary to the first section 31 of the miRNA 33 so as not to be hybridized with the first section 31 of the miRNA 33, from the viewpoint of quantitatively determining the miRNA 33 with high accuracy.

The detection probe 35 forms a stem and loop structure. The stem and loop structure refers to, in a case where there are sequences complementary to each other in two separate regions within a single strand nucleic acid, one having a double stranded structure (stem structure) which is formed through an interaction between pairs of bases of nucleic acids, and a loop structure (also called a hairpin loop) which is formed by a sequence in-between the two regions.

In the present embodiment, the detection probe 35 is constituted of: the two stem sections 35c and 35d forming double strands; the loop section 35e which is a region between the two stem sections 35c and 35d; and the sequence 35b that can be hybridized with the second section 32, from the 5'-protruding terminal side. That is, the detection probe 35 has a 3'-protruding terminus. The detection probe has a protruding terminus, and whether the protruding terminus included in the detection probe is the 5'-protruding terminus or the 3'-protruding terminus depends on whether the capture probe and the substrate bind to each other through the 5'-terminus of the capture probe or through the 3'-terminus of the capture probe.

The length of a stem section in the detection probe 35 is determined by a balance with the length of a loop section. The length thereof is not particularly limited as long as the length thereof is a length in which the detection probe 35 can stably form a stem loop structure, and is preferably 3 bases to 50 bases and more preferably 5 bases to 20 bases.

The length of a loop section in the detection probe 35 is determined by a balance with the length of a stem section. The length thereof is not particularly limited as long as the length thereof is a length in which the detection probe 35 can stably form a stem loop structure, and is preferably 3 bases to 200 bases and more preferably 5 bases to 100 bases.

The length of the detection probe 35 is not particularly limited as long as the length thereof is a length in which it is possible to form a stem loop structure and which is required for functioning as a probe, and is preferably 14 bases to 200 bases and more preferably 24 bases to 150 bases in consideration of the number of bases of the second section 32 and the number of bases required for forming a stem loop structure.

The detection probe 35 may be DNA or RNA. The capture probe is not limited to be a natural one or a non-natural one as long as the probe has the same function as that of DNA or RNA and may be one containing an artificial nucleic acid such as a peptide nucleic acid (PNA), a locked nucleic acid (LNA), and a bridged nucleic acid (BNA). It is preferable that the detection probe 35 contains an LNA or a BNA from the viewpoint of higher affinity to the target miRNA, being more hardly recognized by DNase or RNase, and being more capable of becoming a substrate for DNA ligase such as T4 DNA ligase, compared to DNA or RNA.

It is preferable that at least any one of the capture probe 34 and the detection probe 35 contains an LNA or a BNA and it is more preferable that both of the capture probe 34 and the detection probe 35 contains an LNA or a BNA.

The detection probe 35 is labeled by the labeling substance 35a. Examples of the labeling substance include fluorescent dyes, fluorescent beads, quantum dots, biotin, antibodies, antigens, energy absorption materials, radioisotopes, chemiluminescent bodies, and enzymes.

Examples of the fluorescent dyes include carboxyfluorescein (FAM), 6-carboxy-4',5'-dichloro-2',7'-dimethoxy fluorescein (JOE), fluorescein isothiocyanate (FITC), tetra-chloro-fluorescein (TET), 5'-hexachloro-fluorescein-CE phosphoroamidite (HEX), Cy3, Cy5, Alexa 568, and Alexa 647.

In the total RNA, there is only a minute amount of miRNA, and therefore, it is difficult to label the miRNA at high efficiency without fractionating the miRNA. In contrast, in the present embodiment, a detection probe which has been previously labeled is used, and therefore, it is possible to detect the miRNA with high sensitivity.

In addition, it is preferable that the biomolecule detection unit 4 further comprises a washing solution introduction inlet 4b as shown in FIG. 3. In addition, the biomolecule detection unit 4 comprises a flow path in which a liquid circulates as shown in FIG. 3, and a rotary mixer which is constituted of a pump valve not shown in the drawing.

After the biomolecule is sent to the biomolecule detection unit 4, a detection probe solution is injected into a detection probe introduction inlet 4a after opening a valve 4d.

For example, the detection probe solution includes: 100 nM to 200 nM detection probe, 100 mM to 200 mM Tris-HCl (pH 7.5), 200 mM to 400 mM NaCl, 10 mM to 30 mM $MgCl_2$, 0.5 mg/mL to 2 mg/mL BSA, 10 mM to 30 mM DTT, and 5 units/μL to 20 units/μL T4 DNA Ligase. The detection probe solution is sent for about 30 seconds at a suction pressure of less than or equal to 6 kPa.

Next, the biomolecule and the detection probe solution are circulated and mixed within the biomolecule detection unit. For example, the opening and closing of pump valves which are not shown in the drawing is continuously performed for about 10 minutes. A complex (miRNA 33—detection probe 35—capture probe 34 complex) is efficiently formed on a substrate within a short period of time through the circulation of the liquid (refer to FIGS. 9(A) and 9(B)).

Next, it is preferable to remove a non-specific adsorbed material on a substrate (substrate 4c in FIG. 3) by washing the substrate to which a capture probe is immobilized. A washing solution is injected into the washing solution introduction inlet 4b after opening a valve 4e, and is introduced into the substrate 4c.

For example, the washing solution is a 0.2×SSC buffer of which the amount used is 500 The washing is performed by sending the washing solution for 1 minute at a suction pressure of less than or equal to 6 kPa.

A waste liquid which has been passed through the substrate 4c is sent to the third waste liquid tank 9 after passing through the fifth flow path 12 via the valve 12a.

Next, the intensity of a labeling substance of the complex which has been formed on the substrate 4c is measured. The intensity of a labeling substance reflects the amount of biomolecule present. Therefore, according to the present embodiment, it is possible to quantitatively determine the amount of biomolecule contained in a sample.

The measurement of the intensity of a labeling substance is performed by, for example, a control unit, such as a microscope, a light source, or a personal computer, which are not shown in the drawing.

According to the present embodiment, it is possible to promptly perform analysis of an exosome only within about one hour unlike in the related art in which it has taken one day or longer.

In addition, in the exosome purification unit of this device, after immobilizing an exosome on a substrate as described above, a biomolecule present on the surface of the exosome may be detected in the exosome purification unit.

The method of detecting a biomolecule present on the surface of the exosome which has been immobilized to the substrate comprises: forming a complex by causing an interaction between the biomolecule, which exists on the surface of the exosome, and a first molecule, which specifically binds to the biomolecule; and detecting the complex (first molecule-exosome complex) on the substrate.

The method of detecting the first molecule-exosome complex is, for example, a step of detecting fluorescence of the first molecule-exosome complex which is fluorescently labeled. For example, in a case of using an antibody as a first molecule, it is preferable to use a secondary antibody, against the antibody as the first molecule, which is labeled with enzymes such as peroxidase or alkaline phosphatase, or nanoparticles such as gold colloid or quantum dots.

Examples of the quantum dots include CdSe or CdTe. These quantum dots are excellent in that the quantum dots are not easily photo-bleached compared to organic pigments or fluorescent proteins in the related art.

In addition, a detection method using ELISA may be used. Examples thereof include a method of allowing the enzyme-labeled secondary antibody to act on a primary antibody, adding a chromogenic substrate thereto, and detecting color development of an enzyme reaction product. By way of this, it is possible to detect an exosome similarly to the case of the above-described fluorescent labeling.

The exosome purification unit of this device comprises an inlet for introducing a detection solution which is used to detect a biomolecule on the surface of an exosome. The detection solution is a solution containing a first molecule and a secondary antibody.

The exosome is a secretion of a cell and expresses biomolecules, for example, proteins, nucleic acids, sugar chains, and a sugar lipid, which are derived from the cell of a secretion source, on the surface thereof. An abnormal cell such as a cancer cell existing within a living body expresses specific proteins in a cell membrane thereof.

For this reason, it is possible to detect an abnormality of a cell of a secretion source by analyzing proteins expressed on the surface of the exosome. Here, the surface of the exosome is a membrane surface of a membrane vesicle which is secreted from a cell, and refers to a section on which the secreted exosome comes into contact with the environment within a living body.

Examples of the interaction between a first molecule and an exosome include a binding reaction such as an antigen-antibody reaction.

An abnormal cell secreting an exosome expresses a specific protein as a biomolecule on the surface of the cell, or is deficient in expressing a specific protein on the abnormal cell. Accordingly, it is possible to detect an abnormality in a cell by using, as a first molecule, an antibody against an antigen protein having a different expression pattern compared to the pattern of a normal cell.

From such viewpoint, it is preferable that an antibody to be used binds to proteins which are highly expressed in an abnormal cell or in a normal cell, as an antigen. It is more preferable that an antibody to be used binds to proteins which are specifically expressed in an abnormal cell or in a normal cell, as an antigen.

In addition, as the first molecule, an aptamer is also suitably used without being limited to be an antibody. Examples of the aptamer include a nucleic acid aptamer or a peptide aptamer.

It is possible to analyze an exosome in two steps by performing detection of a biomolecule existing on the surface of the exosome as described above and detection of miRNA included in the exosome thereof, on this device. For example, in a case of breast cancer, a breast cancer cell-derived exosome expresses MUC1, CD24, and ADAM10 as membrane proteins on the surface thereof. An anti-MUC1 antibody, an anti-CD24 antibody, and an anti-ADAM10 antibody respectively bind to these membrane proteins. In addition, miR-1275 and miR21 are included in the breast cancer cell-derived exosome. Accordingly, it is possible to realize an examination with higher accuracy or reliability by analyzing membrane proteins and miRNA using this device in a case of examining breast cancer. Similarly in cases other than the case of breast cancer, this device can analyze an exosome in two steps by detecting membrane proteins on the surface of the exosome and miRNA which is included in the exosome, each corresponding to a disease.

Second Embodiment

Figure 4:
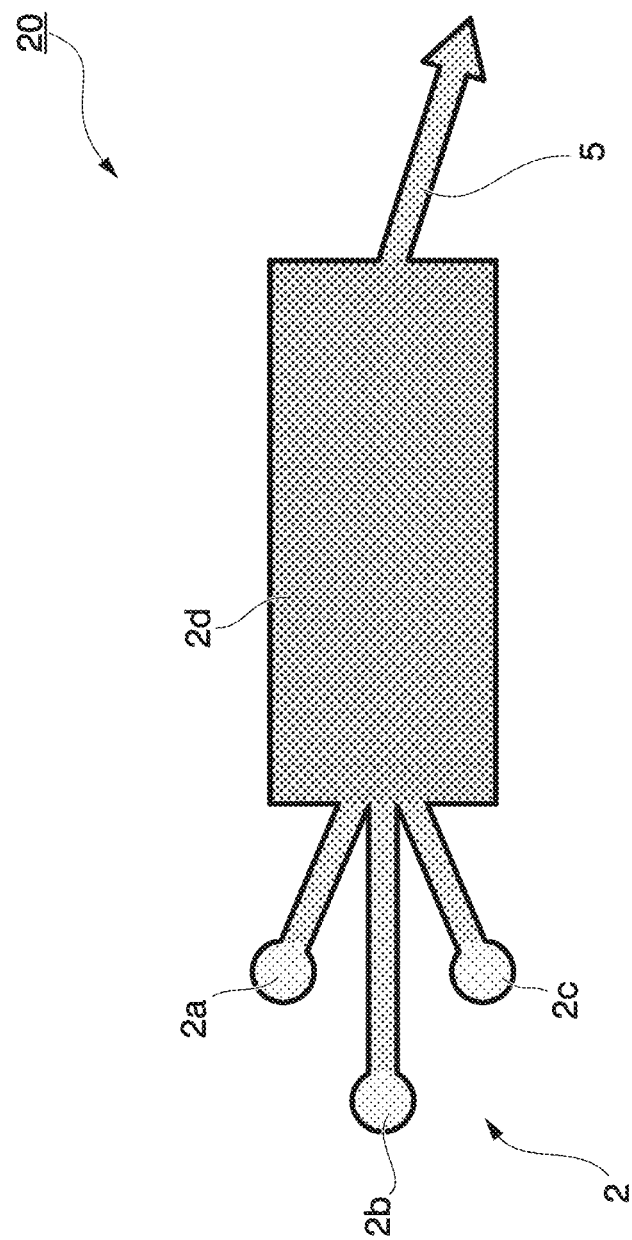
FIG. 4 is a schematic view of an aspect of a fluidic device in the present embodiment.

As shown in FIG. 4, a fluidic device 20 of the present embodiment is a fluidic device, which purifies a biomolecule included in an exosome in a sample, and comprises a sample introduction inlet 2b and an exosome-disrupting liquid introduction inlet 2c; and an exosome immobilization unit 2d which has a layer modified with a compound having a hydrophilic chain and a hydrophobic chain.

In addition, as shown in FIG. 4, it is more preferable that the fluidic device 20 of the present embodiment further comprises a washing solution introduction inlet 2a.

Each configuration in the fluidic device 20 of the present embodiment overlaps with each configuration in the first embodiment, and therefore, the description thereof will not be repeated.

According to the present embodiment, it is possible to simply and efficiently purify a biomolecule in an exosome.
<<Exosome Analysis Method>>

The exosome analysis method of the present embodiment comprises a step of purifying and disrupting an exosome on an exosome purification unit which has a layer modified with a compound having a hydrophilic chain and a hydrophobic chain.

It is preferable that the exosome analysis method of the present embodiment further comprises a step of purifying and detecting a biomolecule released from the disrupted exosome. The detection step may not be performed within the fluidic device. Examples thereof include a step of analyzing a nucleic acid in an exosome using a DNA sequencer.

Other details will not be repeated since these are described in the first embodiment of <<Fluidic device>>.
<<Biomolecule Analysis Method>>

A biomolecule analysis method of the present embodiment comprises: (a) a step of bringing an exosome-containing sample into contact with a substrate which is modified with a compound which has a hydrophobic chain and a hydrophilic chain in a fluidic device, to bond the exosome to the compound which has a hydrophobic chain and a hydrophilic chain on the substrate; (b) a step of releasing a biomolecule contained in the exosome by disrupting the exosome after making a disrupting liquid flow to the substrate to which the exosome is immobilized; (c) a step of purifying the biomolecule; and (d) a step of detecting the biomolecule.

In the biomolecule analysis method of the present embodiment, the analyte is a biomolecule in an exosome. The step (d) may not be performed within the fluidic device. Examples thereof include a step of analyzing a nucleic acid in an exosome using a DNA sequencer.

In addition, it is preferable that the purification step (c) includes (c1) a step of capturing the biomolecule in a capturing unit, and (c2) a step of making the biomolecule flow out of the capturing unit.

In the present embodiment, it is preferable that the step (c1) is a step of sending a disrupting liquid containing a biomolecule which has been obtained in the step (b), to the capturing unit and capturing the biomolecule contained in the disrupting liquid.

The capturing unit is not particularly limited as long as it is possible to capture a biomolecule, and examples thereof include the above-described biomolecule immobilization unit 3c.

In a case of analyzing a biomolecule in a cell, in general, the composition of a disrupting liquid is not the same as that of a capturing liquid to be sent to a capturing unit such as a silica membrane. In many cases, phenol or a surfactant is used in disrupting. However, in this case, it is necessary to additionally mix in ethanol, which is necessary for capturing a biomolecule in the capturing unit. The present inventors have confirmed that it is easy to disrupt an exosome compared to a cell, and therefore, it became possible to perform the disrupting and the capturing at an identical composition in the present embodiment. According to the present embodiment, it is possible to simplify the configuration of the device.

In addition, in the present embodiment, for example, detection of a biomolecule present on the surface of the exosome on a substrate to which the exosome is immobilized is performed.

Other details will not be repeated since these are described in the first embodiment of <<Fluidic device>>.
<<Biomolecule Detection Method>>

A biomolecule detection method of the present embodiment comprises: (a) a step of bringing a sample, which includes a structure surrounded by a lipid bilayer, into contact with a substrate modified with a compound having a hydrophobic chain and a hydrophilic chain, to immobilize the structure surrounded by the lipid bilayer onto the compound having a hydrophobic chain and a hydrophilic chain on the substrate; (b) a step of releasing a biomolecule contained in a membrane vesicle by disrupting the membrane vesicle; and (d) a step of detecting the biomolecule.

In the step (a) according to the present embodiment, the subject is not limited to an exosome. The substrate modified with a compound having a hydrophobic chain and a hydrophilic chain has properties of capturing a lipid bilayer, and therefore, it is also possible to capture a structure, such as a leukocyte, surrounded by a lipid bilayer.

In addition, the disrupting liquid, which disrupts the structure, such as a cell or a leukocyte, surrounded by a lipid bilayer, instead of disrupting an exosome as a subject, is, for example, phenol or a surfactant. In this case, for example, ethanol is additionally mixed in when capturing a nucleic acid included in the structure surrounded by a lipid bilayer, using a silica membrane or the like.

Hereinafter, the present invention will be described using Example, but the present invention is not limited to the following Example.
[Example]
[Purification of Exosome]

A glass surface was modified with 3-aminopropyltriethoxysilane (hereinafter, also referred to as APTES) and was then modified with a PEG-lipid derivative, which immobilized an exosome to the terminus of APTES and was represented by the Formula (1), and methoxy PEG which suppresses non-specific adsorption. An exosome suspension, which was recovered through ultracentrifugation of a culture supernatant of a breast cancer cell strain MCF-7, and exosomes in human serum were immobilized to the inside of the device.

The evaluation of the immmobilization of exosomes was performed by measuring the density of immobilized particles using AFM.

Figure 5:
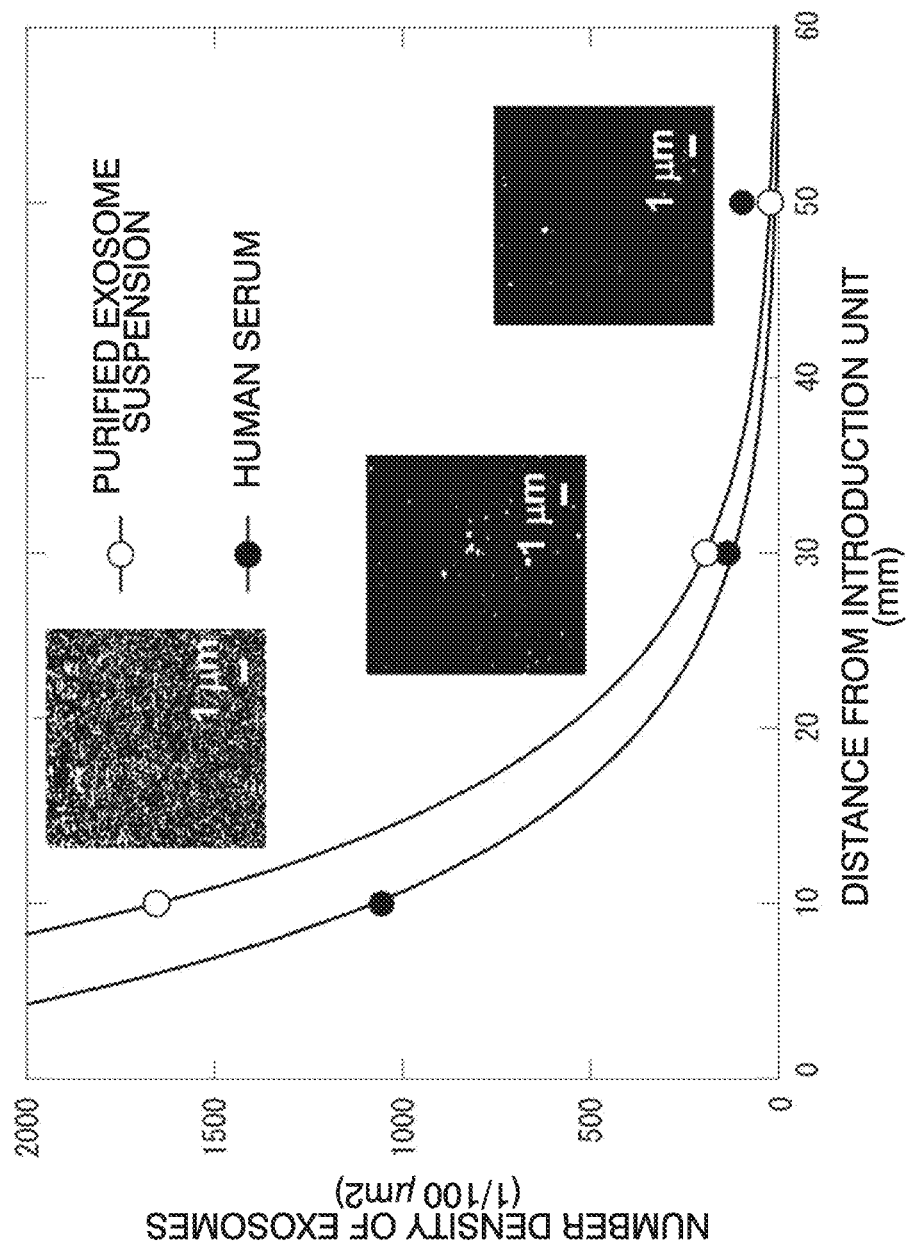
FIG. 5 is a result of quantitative determination of an exosome which is immobilized to a BAM substrate in Example.

AFM images and the immobilization density of exosomes which have been immobilized in the device are shown in FIG. 5. First, it was confirmed that particles having diameters of 30 nm to 200 nm were immobilized thereto, from the AFM images.

Next, it was confirmed that the immobilization density was exponentially decreased with respect to the distance from the immobilization layer. In addition, the immobilized amount in a case where exosomes were directly immobilized from human serum was 74% of cases where purified exosomes were immobilized. Therefore, it was considered that the methoxy PEG contributed to the suppression of the non-specific adsorption.
[Disruption of Exosome]

The efficiency of disrupting an exosome was evaluated by quantitatively determining the amount of miRNA which has been released from the exosome.

The amount of miRNA, which has been released from the exosome by bringing the purified exosome into contact with a disrupting liquid, was obtained through quantitative real-time PCR. In addition, miRNeasy Mini Kit of QIAGEN which is a product of extracting miRNA from a cell was used for the comparison with the efficiency of the disruption. The comparison results of the efficiency of the disruption are shown in FIG. 6.
[Purification of miRNA]

A miniaturized silica membrane was immobilized to the inside of a flow path, and purification of miRNA was performed. An exosome-disrupting liquid containing miRNA passed through the silica membrane through a suction operation. Subsequently, washing and drying of the silica membrane were performed, and then, miRNA was recovered by introducing a miRNA elution liquid. The amount of miRNA recovered was obtained through quantitative real-time PCR. In addition, miRNeasy Mini Kit of QIAGEN was used for the comparison with a general spin column method.

Figure 6:
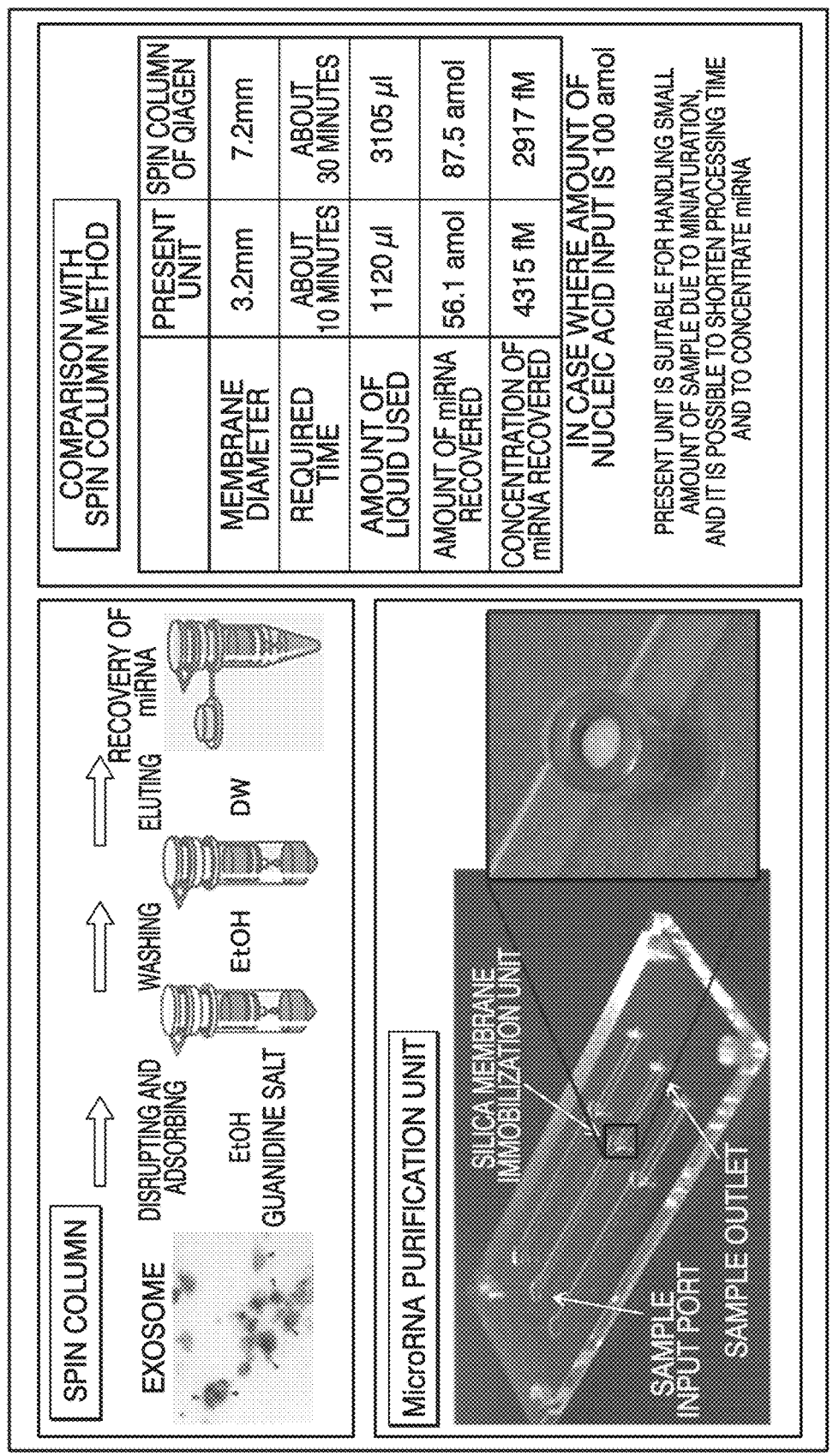
FIG. 6 is a result of quantitative determination of miRNA purified in Example.

The recovery results of miRNA are shown in FIG. 6. In the present unit, shortening of the required time and reduction of the amount of reagent used were achieved by reducing the size of the silica membrane. In addition, it became possible to recover miRNA using a small amount of elution liquid in accordance with the reduction in the size, and therefore, it became possible to concentrate the miRNA solution.
[Detection of miRNA]

This device detects miR-141, miR-143, miR-1275, miR-107, miR-181a-2*, miR-484, miR-21, let-7a, let-7b, let-7d, and let-7f, as target miRNAs. In total 12 kinds of nucleic acid probes of detection probes having a sequence which is complementary to each target miRNA were designed and synthesized. In contrast, capture probes having a sequence complementary to each target miRNA were synthesized on a glass substrate, and were arranged in a spot shape.

miR-141 is contained in a prostatic cancer- or ovarian cancer-derived exosome. miR-143 is contained in a chronic cardiac disease-derived exosome. miR-1275 is contained in a breast cancer-derived exosome. miR-107 is contained in a prostatic cancer- or ovarian cancer-derived exosome. miR-181a-2* is contained in a prostatic cancer-derived exosome. miR-484 is contained in a prostatic cancer- or ovarian cancer-derived exosome. miR-21 is contained in a prostatic cancer-, liver cancer-, ovarian cancer-, breast cancer-, pancreatic cancer-, or lung cancer-derived exosome. let-7a and let-7b are contained in a colorectal cancer-, lung cancer-, stomach cancer-, or ovarian cancer-derived exosome. let-7d and let-7f are contained in a stomach cancer- or ovarian cancer-derived exosome. miR-39 is a nematode-derived control spot.

Sequences of the target miRNA, the capture probes, and the detection probes are shown below.

```
(1) Target miRNA 1: miR-141
[Sequence: 5'-UAACACUGUCUGGUAAAGAUGG-3']
(SEQ ID No: 1: 22-mer)

Target miRNA 2: miR-143
[Sequence: 5'-UGAGAUGAAGCACUGUAGCUC-3']
(SEQ ID No: 2: 21-mer)

Target miRNA 3: miR-1275
[Sequence: 5'-GUGGGGGAGAGGCUGUC-3']
(SEQ ID No: 3: 17-mer)

Target miRNA 4: miR-107
[Sequence: 5'-AGCAGCAUUGUACAGGGCUAUCA-3']
(SEQ ID No: 4: 23-mer)

Target miRNA 5: miR-181a-2*
[Sequence: 5'-ACCACUGACCGUUGACUGUACC-3']
(SEQ ID No: 5: 22-mer)

Target miRNA 6: miR-484
[Sequence: 5'-UCAGGCUCAGUCCCCUCCCGAU-3']
(SEQ ID No: 6: 22-mer)

Target miRNA 7: miR-21
[Sequence: 5'-UAGCUUAUCAGACUGAUGUUGA-3']
(SEQ ID No: 7: 22-mer)

Target miRNA 8: let-7a
[Sequence: 5'-UGAGGUAGUAGGUUGUAUAGUU-3']
(SEQ ID No: 8: 22-mer)

Target miRNA 9: let-7b
[Sequence: 5'-UGAGGUAGUAGGUUGUGUGGUU-3']
(SEQ ID No: 9: 22-mer)

Target miRNA 10: let-7d
[Sequence: 5'-AGAGGUAGUAGGUUGCAUAGUU-3']
(SEQ ID No: 10: 22-mer)

Target miRNA 11: let-7f
[Sequence: 5'-UGAGGUAGUAGAUUGUAUAGUU-3']
(SEQ ID No: 11: 22-mer)

Target miRNA 12: miR-39
[Sequence: 5'-UCACCGGGUGUAAAUCAGCUUG-3']
(SEQ ID No: 12: 22-mer)
```

(2) Capture Probe 1

[Sequence: 5'-p-X1-fS-3']

X1 represents the following sequence, p represents a phosphoric acid, S represents a thiol group, and f represents 6-FAM (6-fluoroscein).

```
X1:
ACCAGACAGTGTTAACAACAACAACAACAACAACAACAACAACAACA
ACAACAACAA (SEQ ID No: 13: 60-mer)

Capture probe 2
X1:
GTGCTTCATCTCAACAACAACAACAACAACAACAACAACAACAACAA
CAACAACAAC (SEQ ID No: 14: 60-mer)

Capture probe 3
X1:
CTCCCCCACACAACAACAACAACAACAACAACAACAACAACAACAAC
AACAACAACA (SEQ ID No: 15: 60-mer)

Capture probe 4
X1:
CTGTACAATGCTGCTACAACAACAACAACAACAACAACAACAACAAC
AACAACAACA (SEQ ID No: 16: 60-mer)

Capture probe 5
X1:
CAACGGTCAGTGGTACAACAACAACAACAACAACAACAACAACAACA
ACAACAACAA (SEQ ID No: 17: 60-mer)

Capture probe 6
X1:
GGGACTGAGCCTGAACAACAACAACAACAACAACAACAACAACAACA
ACAACAACAA (SEQ ID No: 18: 60-mer)

Capture probe 7
X1:
AGTCTGATAAGCTAACAACAACAACAACAACAACAACAACAACAACA
ACAACAACAA (SEQ ID No: 19: 60-mer)

Capture probe 8
X1:
AACCTACTACCTCAACAACAACAACAACAACAACAACAACAACAACA
ACAACAACAA (SEQ ID No: 20: 60-mer)

Capture probe 9
X1:
ACCTACTACCTCAACAACAACAACAACAACAACAACAACAACAACAA
CAACAACAAC (SEQ ID No: 21: 60-mer)

Capture probe 10
X1:
AACCTACTACCTCTACAACAACAACAACAACAACAACAACAACAACA
ACAACAACAA (SEQ ID No: 22: 60-mer)

Capture probe 11
X1:
ATCTACTACCTCAACAACAACAACAACAACAACAACAACAACAACAA
CAACAACAAC (SEQ ID No: 23: 60-mer)

Capture probe 12
X1:
TTTACACCCGGTGAACAACAACAACAACAACAACAACAACAACAACA
ACAACAACAA (SEQ ID No: 24: 60-mer)
```

(3) Detection Probe 1

[Sequence: 5'-p-X2-Al-X3-3']

X2 and X3 represent the following sequences, p represents a phosphoric acid, and Al represents Alexa647-AminoC6-dA.

```
X2:
CTCAACTGGTGTCGTGG
(SEQ ID No: 25: 17-mer)

X3:
GTCGGCAATTCAGTTGAGCCATCTTT
(SEQ ID No: 26: 26-mer)

Detection probe 2
X2:
CTCAACTGGTGTCGTGG
(SEQ ID No: 25: 17-mer)

X3:
GTCGGCAATTCAGTTGAGGAGCTACA
(SEQ ID NO: 27: 26-mer)

Detection probe 3
X2:
CTCAACTGGTGTCGTGG
(SEQ ID No: 25: 17-mer)

X3:
GTCGGCAATTCAGTTGAGGACAGCCT
(SEQ ID NO: 28: 26-mer)
```

```
-continued
Detection probe 4
X2:
CTCAACTGGTGTCGTGG
(SEQ ID No: 25: 17-mer)

X3:
GTCGGCAATTCAGTTGAGTGATAGCC
(SEQ ID NO: 29: 26-mer)

Detection probe 5
X2:
CTCAACTGGTGTCGTGG
(SEQ ID No: 25: 17-mer)

X3:
GTCGGCAATTCAGTTGAGGGTACAGT
(SEQ ID NO: 30: 26-mer)

Detection probe 6
X2:
CTCAACTGGTGTCGTGG
(SEQ ID No: 25: 17-mer)

X3:
GTCGGCAATTCAGTTGAGATCGGGAG
(SEQ ID NO: 31: 26-mer)

Detection probe 7
X2:
CTCAACTGGTGTCGTGG
(SEQ ID No: 25: 17-mer)

X3:
GTCGGCAATTCAGTTGAGTCAACATC
(SEQ ID NO: 32: 26-mer)

Detection probe 8
X2:
CTCAACTGGTGTCGTGG
(SEQ ID No: 25: 17-mer)

X3:
GTCGGCAATTCAGTTGAGAACTATAC
(SEQ ID NO: 33: 26-mer)

Detection probe 9
X2:
CTCAACTGGTGTCGTGG
(SEQ ID No: 25: 17-mer)

X3:
GTCGGCAATTCAGTTGAGAACCACACA
(SEQ ID NO: 34: 27-mer)

Detection probe 10
X2:
CTCAACTGGTGTCGTGG
(SEQ ID No: 25: 17-mer)

X3:
GTCGGCAATTCAGTTGAGAACTATGC
(SEQ ID NO: 35: 26-mer)

Detection probe 11
X2:
CTCAACTGGTGTCGTGG
(SEQ ID No: 25: 17-mer)

X3:
GTCGGCAATTCAGTTGAGAACTATACA
(SEQ ID NO: 36: 27-mer)

Detection probe 12
X2:
CTCAACTGGTGTCGTGG
(SEQ ID No: 25: 17-mer)

X3:
GTCGGCAATTCAGTTGAGCAAGCTGA
(SEQ ID NO: 37: 26-mer)
```

A DNA micro array substrate to which the above-described capture probes were immobilized was allowed to stand for 90 minutes at room temperature while being brought into contact with a solution in Table 1. After washing the DNA micro array substrate with ultrapure water and drying the DNA micro array substrate, the DNA micro array substrate was installed in a rotary mixer (biomolecule detection unit).

In Table 1, the composition of Takara 10× buffer is 500 mM Tris-HCl (pH 7.5), 100 mM MgCl2, and 50 mM DTT.

TABLE 1

| | |
|---|---|
| 10 unit/μl T4 Polynucleotide Kinase | 25 μl |
| 5M betaine 100 mM ATP | 10 μl |
| Takara 10 × buffer | 100 μl |
| Milli-Q Water | 865 μl |
| Total | 1000 μl |

Furthermore, a miRNA solution with an arbitrary concentration was prepared as in Table 2, and a hybridization reaction solution containing a detection probe 1 was prepared as in Table 3.

TABLE 2

| | |
|---|---|
| 1 μM miR-141 | 1 μl |
| 1 μM miR-143 | 1 μl |
| 1 nM miR-1275 | 1 μl |
| 1 μM miR-107 | 1 μl |
| 1 μM miR-181a-2* | 1 μl |
| 1 μM miR-484 | 1 μl |
| 1 μM miR-21 | 1 μl |
| 1 μM let-7a | 1 μl |
| 1 μM let-7b | 1 μl |
| 1 μM let-7d | 1 μl |
| 1 μM let-7f | 1 μl |
| 10 μM miR-39 | 1 μl |
| RNase-free water | 88 μl |
| Total | 100 μl |

TABLE 3

| | |
|---|---|
| 20 μM Detect probe1 | 1 μl |
| 20 μM Detect probe2 | 1 μl |
| 20 μM Detect probe3 | 1 μl |
| 20 μM Detect probe4 | 1 μl |
| 20 μM Detect probe5 | 1 μl |
| 20 μM Detect probe6 | 1 μl |
| 20 μM Detect probe7 | 1 μl |
| 20 μM Detect probe8 | 1 μl |
| 20 μM Detect probe9 | 1 μl |
| 20 μM Detect probe10 | 1 μl |
| 20 μM Detect probe11 | 1 μl |
| 20 μM Detect probe12 | 1 μl |
| 1M Tris-HCl (pH 7.5) | 13.3 μl |
| 1M $MgCl_2$ | 2 μl |
| 100 mM ATP | 2 μl |
| 10 mg/ml BSA | 2 μl |
| 1M DTT | 2 μl |
| 2.5M NaCl | 12 μl |
| 350 units/μl T4 DNA ligase | 2.9 μl |
| RNase-free water | 51.8 μl |
| Total | 100 μl |

The prepared miRNA solution and the hybridization reaction solution were respectively introduced into separate inlets, and the solutions were hybridized by being circulated for 10 minutes in the rotary mixer.

After the completion of the hybridization reaction, the DNA micro array substrate was washed by making 500 μl of a washing solution, which contains 0.3 M NaCl and 30 mM sodium citrate, flow from each of the above-described inlets, and the fluorescence intensity was measured after observing the substrate using a fluorescence microscope.

Figures 7A, 7B:
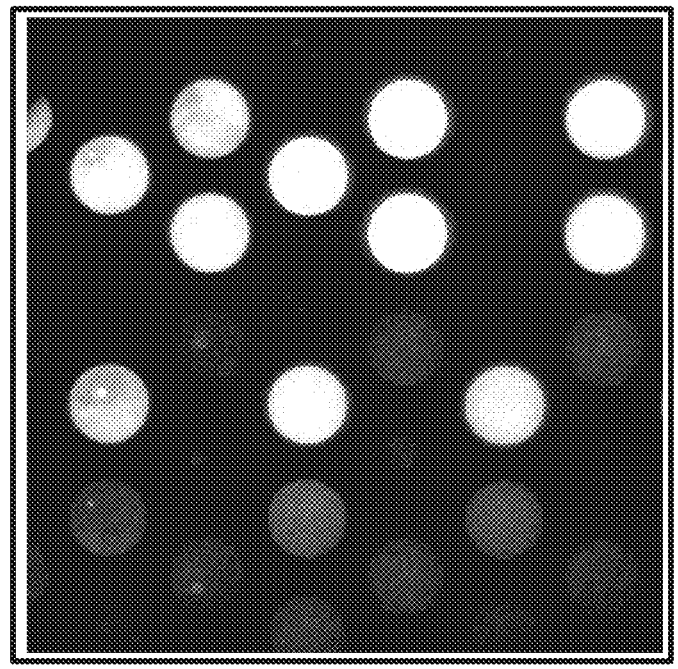
FIG. 7A is a result of detection of miRNA using a fluidic device which has a detection unit including a substrate to which a probe complementary to miRNA is immobilized in Example.
FIG. 7B is a view showing a spot which corresponds to a spot of the image of FIG. 7(A) and in which fluorescence is to be observed. In the drawing, the spot shown by half-tone dot meshing is a spot which corresponds to target miRNA. Each alphabet corresponds to the following miRNA: A: 141, B: 143, C: 1275, D: 107, E: 181a-2*, F: 484, S: let-7a, T: let-7b, U: let-7d.
Figure 8:
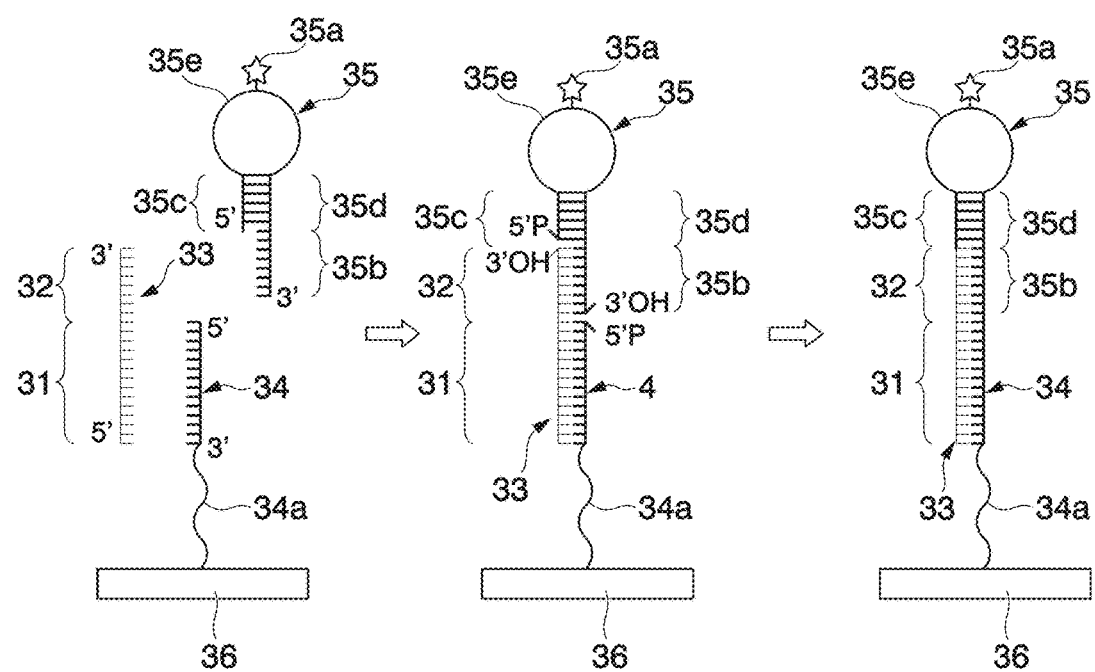
FIG. 8 is a schematic view of an aspect of a substrate of a fluidic device in the present embodiment.

The results are shown in FIGS. 7(A) and 7(B). FIG. 7(A) is an image of the substrate showing miRNA detection results. Spots in FIG. 7(B) correspond to spots of the image in FIG. 7(A), and a spot shown by half-tone dot meshing is a spot which corresponds to target miRNA and in which fluorescence is to be observed. Each alphabet corresponds to the following miRNA:

A: 141, B: 143, C: 1275, D: 107, E: 181a-2*, F: 484, S: let-7a, T: let-7b, U: let-7d.

In each of the spots to which probes corresponding to the introduced miRNA were immobilized, fluorescence images of the detection probes which had been labeled with Alexa 647 were observed. miR-1275 of "C" was placed in a concentration of one thousandth of another miRNA in order to check the detection limit concentration, and therefore, the fluorescence became dark. In addition, the difference in brightness for each of the sequences of the probes is caused by the difference in affinity of probes.

For this reason, it was confirmed that it was possible to sequence-dependently detect miRNA.

[Opening and Closing of Valve in Fluidic Device]

A schematic view of a fluidic device for describing an opening/closing operation of a valve in this Example is shown in FIG. 9(A). This device comprises an exosome purification unit (exosome purification unit 2), a miRNA purification unit (biomolecule purification unit 3), a DNA chip (biomolecule detection unit 4), a waste liquid tank 7, a waste liquid tank 8, and a waste liquid tank 9. The waste liquid tanks comprises a suction port.

It was confirmed that it was possible to control the flow of a fluid through the control of the opening and closing of valves in each step shown in FIG. 9(B). For example, when introducing a supernatant, a solution from a suction port A of a supernatant waste liquid tank is suctioned after opening a valve No. 1 (1), a valve No. 3 (3), a valve No. 5 (5), a valve No. 7 (7), a valve No. 8 (8), a valve No. 10 (10), and a valve No. 13 (13) in FIG. 9(A).

From the above-described results, according to the present embodiments, it is possible to analyze the content of an exosome in a series of flows by introducing a sample into the device.

EXPLANATION OF REFERENCES 1, 20 . . . fluidic device, 2 . . . exosome purification unit, 2a . . . washing solution introduction inlet, 2b . . . sample introduction inlet, 2c . . . disrupting liquid introduction inlet, 2d . . . exosome immobilization unit, 2e, 2f, 2g, 3d, 3f, 5a, 10a, 11a . . . valve, 2h, 2i, 2j, 3e, 3g . . . flow path, 3 . . . biomolecule purification unit, 3b . . . biomolecule recovery liquid introduction inlet, 3c . . . biomolecule immobilization unit, 4 . . . biomolecule detection unit, 4a . . . detection probe introduction inlet, 4b . . . washing solution introduction inlet, 4c . . . substrate, 5 . . . first flow path, 6 . . . second flow path, 7 . . . first waste liquid tank, 8 . . . second waste liquid tank, 9 . . . third waste liquid tank, 10 . . . third flow path, 11 . . . fourth flow path, 12 . . . fifth flow path, 33 . . . miRNA, 31 . . . first section, 32 . . . second section, 34 . . . capture probe, 34a . . . spacer, 35 . . . detection probe, 35a . . . labeling substance, 35b . . . sequence, 35c, 35d . . . stem section, 36 . . . substrate

What is claimed is:

1. A fluidic device for detecting a biomolecule contained in an exosome in a sample, comprising:
   an exosome purification unit having an exosome immobilization unit which has a layer modified with a compound having a hydrophobic chain and a hydrophilic chain, wherein the compound is configured to bind to the exosome;
   a biomolecule purification unit;
   a biomolecule detection unit;
   a first flow path which connects the exosome purification unit to the biomolecule purification unit; and
   a second flow path which connects the biomolecule purification unit to the biomolecule detection unit;
   wherein the biomolecule is miRNA;
   wherein the biomolecule detection unit comprises:
   a substrate to which a capture probe including a sequence that can be hybridized with the first section is immobilized in a case where a target miRNA comprises a first section and a second section; and
   a detection probe introduction inlet;
   the detection probe having:
      two stem sections forming a double stranded structure,
      a loop section which is a region between the two stem sections and being labeled using a labeling substance, and
      a 5'-protruding terminus or a 3'-protruding terminus, which has a sequence that can be hybridized with the second section of the target miRNA, and is protruding when the two stem sections form a double chain.

2. The fluidic device according to claim 1, wherein immobilization and disruption of the exosome is performed in the exosome purification unit.

3. The fluidic device according to claim 2, wherein a biomolecule present on the surface of the exosome is detected in the exosome purification unit after the immobilization of the exosome thereto.

4. The fluidic device according to claim 1, wherein the exosome purification unit comprises:
an inlet.

5. The fluidic device according to claim 4, wherein the exosome purification unit comprises
a sample introduction inlet and an exosome-disrupting liquid introduction inlet.

6. The fluidic device according to claim 4, wherein the exosome purification unit comprises a washing solution introduction inlet.

7. The fluidic device according to claim 1, wherein a ceiling height of the exosome immobilization unit is smaller than a ceiling height of the first flow path.

8. The fluidic device according to claim 1, wherein the first flow path is a flow path which sends the exosome-disrupting liquid containing the biomolecule to the biomolecule purification unit from the exosome purification unit, and
wherein the second flow path is a flow path which sends a solution containing the purified biomolecule to the biomolecule detection unit.

9. The fluidic device according to claim 1, further comprising:
a waste liquid tank for each of the exosome purification unit, the biomolecule purification unit, and the biomolecule detection unit, each of the waste liquid tank having an inlet for suctioning;
a third flow path which connects the waste liquid tank for the exosome purification unit to the exosome purification unit;
a fourth flow path which connects the waste liquid tank for the biomolecule purification-unit to the biomolecule purification unit; and
a fifth flow path which connects the waste liquid tank for the biomolecule detection unit to the biomolecule detection unit.

10. The fluidic device according to claim 1,
wherein the biomolecule purification unit comprises:
a biomolecule recovery liquid introduction inlet, and
a biomolecule immobilization unit.

11. The fluidic device according to claim 1,
wherein the exosome purification unit comprises an introduction inlet for a detection solution which is used to detect a biomolecule on the surface of an exosome.

12. A method of analyzing an exosome comprising:
providing the fluidic device of claim 1; and
purifying and disrupting an exosome on the exosome purification unit of the fluidic device.

13. The method of analyzing an exosome according to claim 12, further comprising:
purifying and detecting a biomolecule released from the disrupted exosome.

* * * * *

```
                        SEQUENCE LISTING

<160> NUMBER OF SEQ ID NOS: 37

<210> SEQ ID NO 1
<211> LENGTH: 22
<212> TYPE: RNA
<213> ORGANISM: Homo sapiens
<220> FEATURE:

<400> SEQUENCE: 1
uaacacuguc ugguaaagau gg                                            22

<210> SEQ ID NO 2
<211> LENGTH: 21
<212> TYPE: RNA
<213> ORGANISM: Homo sapiens
<220> FEATURE:

<400> SEQUENCE: 2
ugagaugaag cacuguagcu c                                             21

<210> SEQ ID NO 3
<211> LENGTH: 17
<212> TYPE: RNA
<213> ORGANISM: Homo sapiens
<220> FEATURE:

<400> SEQUENCE: 3 guggggggaga ggcuguc                                                 17
```

```
<210> SEQ ID NO 4
<211> LENGTH: 23
<212> TYPE: RNA
<213> ORGANISM: Homo sapiens
<220> FEATURE:

<400> SEQUENCE: 4
agcagcauug uacagggcua uca                                              23

<210> SEQ ID NO 5
<211> LENGTH: 22
<212> TYPE: RNA
<213> ORGANISM: Homo sapiens
<220> FEATURE:

<400> SEQUENCE: 5
accacugacc guugacugua cc                                               22

<210> SEQ ID NO 6
<211> LENGTH: 22
<212> TYPE: RNA
<213> ORGANISM: Homo sapiens
<220> FEATURE:

<400> SEQUENCE: 6
ucaggcucag uccccucccg au                                               22

<210> SEQ ID NO 7
<211> LENGTH: 22
<212> TYPE: RNA
<213> ORGANISM: Homo sapiens
<220> FEATURE:

<400> SEQUENCE: 7
uagcuuauca gacugauguu ga                                               22

<210> SEQ ID NO 8
<211> LENGTH: 22
<212> TYPE: RNA
<213> ORGANISM: Homo sapiens
<220> FEATURE:

<400> SEQUENCE: 8
ugagguagua gguuguauag uu                                               22

<210> SEQ ID NO 9
<211> LENGTH: 22
<212> TYPE: RNA
<213> ORGANISM: Homo sapiens
<220> FEATURE:

<400> SEQUENCE: 9
ugagguagua gguugugugg uu                                               22

<210> SEQ ID NO 10
<211> LENGTH: 22
<212> TYPE: RNA
<213> ORGANISM: Homo sapiens
<220> FEATURE:

<400> SEQUENCE: 10
agagguagua gguugcauag uu                                               22
```

```
<210> SEQ ID NO 11
<211> LENGTH: 22
<212> TYPE: RNA
<213> ORGANISM: Homo sapiens
<220> FEATURE:

<400> SEQUENCE: 11
ugagguagua gauuguauag uu                                              22

<210> SEQ ID NO 12
<211> LENGTH: 22
<212> TYPE: RNA
<213> ORGANISM: Homo sapiens
<220> FEATURE:

<400> SEQUENCE: 12
ucaccgggug uaaaucagcu ug                                              22

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: Capture
      probe1.

<400> SEQUENCE: 13
accagacagt gttaacaaca acaacaacaa caacaacaac aacaacaaca acaacaaca      60

<210> SEQ ID NO 14
<211> LENGTH: 60
<212> TYPE: DNA
<213> ORGANISM: Artificial Sequence
<220> FEATURE:
<223> OTHER INFORMATION: Description of Artificial Sequence: Capture
      probe2.

<400> SEQUENCE: 14
gtgcttcatc tcaacaacaa caacaacaac aacaacaaca acaacaacaa caacaacaac      60

<210> SEQ ID NO 15
<211> LENGTH: 60
<212> TYPE: DNA
<213> ORGANISM: Artificial Sequence
<220> FEATURE:
<223> OTHER INFORMATION: Description of Artificial Sequence: Capture
      probe3.

<400> SEQUENCE: 15
ctcccccaca caacaacaac aacaacaaca acaacaacaa caacaacaac aacaacaaca      60

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence: Capture
      probe4.

<400> SEQUENCE: 16
ctgtacaatg ctgctacaac aacaacaaca acaacaacaa caacaacaac aacaacaaca      60

<210> SEQ ID NO 17
<211> LENGTH: 60
<212> TYPE: DNA
<213> ORGANISM: Artificial Sequence
```

```
<220> FEATURE:
<223> OTHER INFORMATION: Description of Artificial Sequence: Capture
      probe5.

<400> SEQUENCE: 17
caacggtcag tggtacaaca acaacaacaa caacaacaac aacaacaaca acaacaacaa      60

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: Capture
      probe6.

<400> SEQUENCE: 18
gggactgagc ctgaacaaca acaacaacaa caacaacaac aacaacaaca acaacaacaa      60

<210> SEQ ID NO 19
<211> LENGTH: 60
<212> TYPE: DNA
<213> ORGANISM: Artificial Sequence
<220> FEATURE:
<223> OTHER INFORMATION: Description of Artificial Sequence: Capture
      probe7.

<400> SEQUENCE: 19
agtctgataa gctaacaaca acaacaacaa caacaacaac aacaacaaca acaacaacaa      60

<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence: Capture
      probe8.

<400> SEQUENCE: 20
aacctactac ctcaacaaca acaacaacaa caacaacaac aacaacaaca acaacaacaa      60

<210> SEQ ID NO 21
<211> LENGTH: 60
<212> TYPE: DNA
<213> ORGANISM: Artificial Sequence
<220> FEATURE:
<223> OTHER INFORMATION: Description of Artificial Sequence: Capture
      probe9.

<400> SEQUENCE: 21
acctactacc tcaacaacaa caacaacaac aacaacaaca acaacaacaa caacaacaac      60

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence: Capture
      probe10.

<400> SEQUENCE: 22
aacctactac ctctacaaca acaacaacaa caacaacaac aacaacaaca acaacaacaa      60

<210> SEQ ID NO 23
<211> LENGTH: 60
<212> TYPE: DNA
<213> ORGANISM: Artificial Sequence
```

```
<220> FEATURE:
<223> OTHER INFORMATION: Description of Artificial Sequence: Capture
      probe11.

<400> SEQUENCE: 23
atctactacc tcaacaacaa caacaacaac aacaacaaca caacaacaa caacaacaac      60

<210> SEQ ID NO 24
<211> LENGTH: 60
<212> TYPE: DNA
<213> ORGANISM: Artificial Sequence
<220> FEATURE:
<223> OTHER INFORMATION: Description of Artificial Sequence: Capture
      probe12.

<400> SEQUENCE: 24
tttacacccg gtgaacaaca acaacaacaa caacaacaac aacaacaaca acaacaacaa      60

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: Detect
      probe1-1.

<400> SEQUENCE: 25
ctcaactggt gtcgtgg                                                    17

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Detect
      probe1-2.

<400> SEQUENCE: 26
gtcggcaatt cagttgagcc atcttt                                          26

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Detect
      probe2-2.

<400> SEQUENCE: 27
gtcggcaatt cagttgagga gctaca                                          26

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Detect
      probe3-2.

<400> SEQUENCE: 28
gtcggcaatt cagttgagga cagcct                                          26

<210> SEQ ID NO 29
<211> LENGTH: 26
<212> TYPE: DNA
<213> ORGANISM: Artificial Sequence
```

```
<220> FEATURE:
<223> OTHER INFORMATION: Description of Artificial Sequence: Detect
      probe4-2.

<400> SEQUENCE: 29
gtcggcaatt cagttgagtg atagcc                                            26

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Detect
      probe5-2.

<400> SEQUENCE: 30
gtcggcaatt cagttgaggg tacagt                                            26

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Detect
      probe6-2.

<400> SEQUENCE: 31
gtcggcaatt cagttgagat cgggag                                            26

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Detect
      probe7-2.

<400> SEQUENCE: 32
gtcggcaatt cagttgagtc aacatc                                            26

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Detect
      probe8-2.

<400> SEQUENCE: 33
gtcggcaatt cagttgagaa ctatac                                            26

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Detect
      probe9-2.

<400> SEQUENCE: 34
gtcggcaatt cagttgagaa ccacaca                                           27

<210> SEQ ID NO 35
<211> LENGTH: 26
<212> TYPE: DNA
<213> ORGANISM: Artificial Sequence
```

```
<220> FEATURE:
<223> OTHER INFORMATION: Description of Artificial Sequence: Detect
      probe10-2.

<400> SEQUENCE: 35
gtcggcaatt cagttgagaa ctatgc                                          26

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Detect
      probe11-2.

<400> SEQUENCE: 36
gtcggcaatt cagttgagaa ctataca                                         27

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: Detect
      probe12-2.

<400> SEQUENCE: 37
gtcggcaatt cagttgagca agctga                                          26
```